April 28, 1964 L. CHIARAPPA Plant Pat. 2,397
GRAPEVINE
Filed Oct. 30, 1962
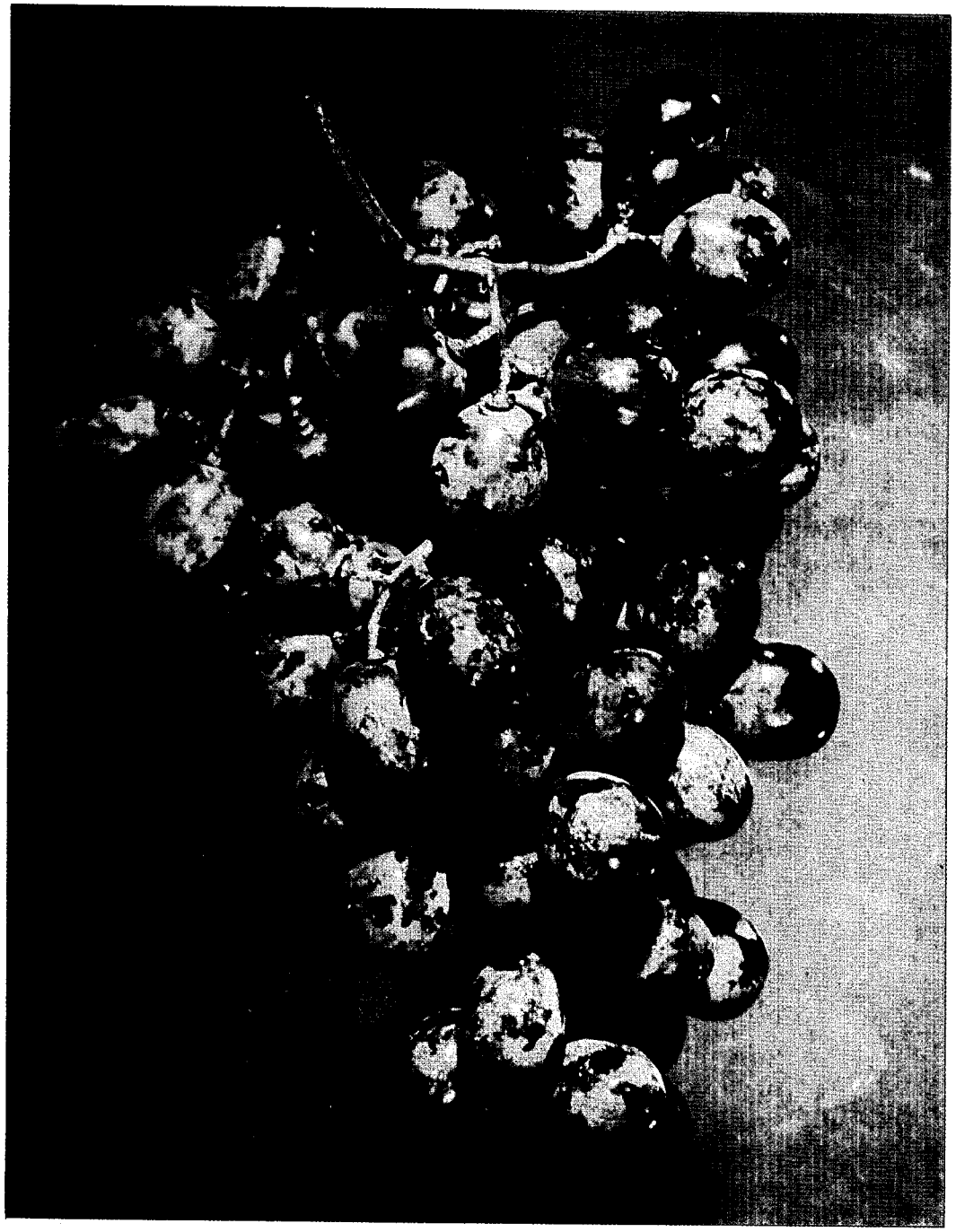
INVENTOR.
LUIGI CHIARAPPA
BY
Flehr and Swan
ATTORNEYS United States Patent Office Plant Pat. 2,397
Patented Apr. 28, 1964

2,397
GRAPEVINE

Luigi Chiarappa, Di Giorgio, Calif., assignor to Di Giorgio Fruit Corporation, San Francisco, Calif., a corporation of Delaware Filed Oct. 30, 1962, Ser. No. 234,268
1 Claim. (Cl. Plt.—47)

This invention relates to a new variety of grape and more particularly to a variety of table grape of the Vinifera type.

The variety is similar to the Emperor but earlier in maturity having berries which are larger, firmer and more uniformly colored. Moreover, there is some similarity to the Queen as far as time of maturity, but the berries are firmer, more strongly attached to the capstems and are more rounded.

The grape was originally discovered by me as a seedling in Tulare County, California.

The new variety has been asexually reproduced by cuttings and layering and the characteristics defined herein below have thereby been found to be permanent.

The accompanying drawing illustrates a typical cluster of the grapes of the variety defined in this invention. The drawing together with the following description, sets forth the characteristics of the new variety of this invention.

The growth habit of the new variety is similar to that of Queen. A high trellis is necessary for supporting its spread-out growth. Vine growth is rapid. New shoots are reddish green or entirely red at the base and green toward the apex. The color of mature cane bark is light brown. Canes are nearly round in cross section and have nodes which are prominent and separated four to six inches apart.

Tendrils are fourteen to sixteen inches long, frequently branched, green in color and with red striations at the base. They appear opposite to a leaf at every other node starting from the fifth or sixth one.

Trunk size is large, measuring up to six inches in circumference at one foot from soil level.

Flowers are perfect in that they include both pistil and stamens. The stamens are five in number, erect and produce abundant pollen. Flowering (in Tulare County, California) starts May 10th to 15th and lasts for seven to ten days.

Leaves are large, particularly at the base of each shoot where their largest diameter measures six to eight inches. They are elongated and lobed with the petiole sinus open and moderately lyre-shaped. The upper leaf area is dark green in color (as the Emperor), while the lower leaf area is Cypress and Forest Green (A Dictionary of Color, Maerz and Paul, McGraw-Hill, 1950, L6, Plate 23). Veins are raised, colored at the base and lacking hairs. Leaf texture is tough, moderately stiff and with a rough surface. Leaf petiole is five to six inches long, red in color with green striations.

The fruit cluster has an average length of nine inches with a maximum of thirteen and a minimum of six inches. The average width in the largest area is five inches, with a maximum of seven and a minimum of four inches. The average cluster weight is 550 grams with a maximum of 900 grams and a minimum of 300 grams. Each cluster is composed of an average of 105 berries with a maximum of 190 and a minimum of sixty berries. Clusters are loose, conically shaped, well filled and with very few or no, shot berries. There is an average of two clusters on each cane. These clusters are produced at the third and fourth nodes. The stem length of the clusters is approximately two inches.

The brush size is fairly long, measuring on the average of four and one-half millimeters and is greenish yellow in color. Capstems are well developed, requiring a force of approximately 330 grams to detach the berry from the supporting capstems.

The berry shape is that of a prolate ellipsoid with the larger diameters measuring about three-quarters of an inch and one inch. The color, in the sun, of fully matured berries is Andorra Red (aforementioned Dictionary of Color, L2 and L4, Plate 8). In a few cases the berry stem ends may remain Holly Green in color (aforementioned Dictionary of Color, L1, Plate 23). The skin is tough and measures 0.16 millimeter in thickness. It does not separate as easily from the pulp as that of the Emperor variety. Seeds are three in number and are fairly large, measuring about seven millimeters in length. The berry flesh is white, exceptionally firm and crisp with a medium juice content. The sugar, at maturity, runs from seventeen to nineteen degrees Balling. The good eating quality of this variety is due to a well balanced sugar/acid ratio.

The ripening period in Tulare County, California, is about September 1st, if vines are not girdled. By gridling, ripening can be anticipated approximately ten to fifteen days. The fruit can remain on the vine for a few weeks without any adverse effect on quality.

The primary use for this variety of grape is for the table. Packing house and vineyard culls can also be used for wine making. Storage quality is good for four months when maintained under refrigeration.

The fruit of this variety of grape is similar in general appearance to the parent vines Emperor and Queen. The main differences are substantially as set forth below.

The berries are less elongated and wider than either of the parent varieties, but the berry firmness is greater.

Skin pigments are more evenly distributed throughout the berry surface, resulting in a more uniform color. At the proper stage of maturity, the red color is greater than that of either the Emperor or the Queen. Coloring may become darker than that of either parent in overripe fruit.

Clusters are slightly smaller than those of the parent vines but are more compact and have less shot berries. Sugar content is not different from that of the Emperor or Queen but a superior eating quality results from what appears to be a more balanced ratio of sugars and acids.

Storage quality is as good as that of the Emperor when fruit stems are properly matured at harvest. Shipping quality is superior to that of Queen because of stronger berry attachment and less brittle stems.

Fruit bearing is not as variable from year to year as is that of the Emperor. Bearing is not as heavy as the Queen and does not require thinning.

The fruit ripens approximately one month earlier than Emperor and one to two weeks after the Queen.

The grape and plant above described, as is apparent, may vary silghtly in details upon various conditions of weather, soil, etc.

I claim:

A new and distinct variety of grape plant substantially as herein shown and described, characterized by its early maturity, large, firm and uniformly colored fruit strongly attached to the capstems.

No references cited.